United States Patent [19]

Moon

[11] Patent Number: 4,918,099

[45] Date of Patent: Apr. 17, 1990

[54] DRUG, PREPARATION AND USE THEREOF

[76] Inventor: Chang-Kiu Moon, Hyundae-villa 101 Ho, Daechi-Dong, Kungnam-Gu, Seoul, Rep. of Korea

[21] Appl. No.: 844,325

[22] Filed: Mar. 26, 1986

[30] Foreign Application Priority Data

Mar. 29, 1985 [DE] Fed. Rep. of Germany ....... 3511609

[51] Int. Cl.$^4$ .............................................. A61K 31/35
[52] U.S. Cl. .................................. 514/453; 514/822; 514/833; 514/866; 514/884
[58] Field of Search ...................... 424/195.1; 514/453, 514/822, 833, 866, 884

[56] References Cited

U.S. PATENT DOCUMENTS

| 4,147,691 | 4/1979 | Montgomery et al. | 260/112 R |
| 4,363,669 | 12/1982 | Cottrell et al. | 106/208 |
| 4,569,839 | 2/1986 | Grollier et al. | 424/74 |

FOREIGN PATENT DOCUMENTS 1281526 7/1972 United Kingdom .

OTHER PUBLICATIONS

Planta Med 66-7 (1985) "Inhibition of Lens-Aldoes Reductase Activity by Brazilin and Hematoxylin".
Planta Med 31 214–20 (1977) Anti-inflammatory Principles of Caesalpinia and Haematoxylan.
Steinmetz, Codex Vegetabilis, 1957, No. 212–216.
Lewis, Medical Botany, 1977, pp. 245 and 375.
The Dispensatory of the U.S.A., 23rd Ed. 1943, Brazil--wood, pp. 1290–1291.
Merck Index, Nos. 1380, 4493 & 4496, 1976.
Altschul, Drugs and Foods from Little-Known Plants, 1973, Nos. 1709–1716.
Chem. Absts. 102: 130972d, 1985.
Moon et al, Planta Med. 66–7 (1985).

Primary Examiner—John W. Rollins
Attorney, Agent, or Firm—Pollock, Vande Sande & Priddy

[57] ABSTRACT

A novel drug comprises as active ingredient an extract extractable from plant material of plants belonging to the genus Caesalpinia, one or several components of this extract and/or one or several substances present in this extract or derived therefrom but prepared synthetically.

These substances are in particular benz(b)indeno(2.1-d)pyran derivatives, including brazilin, brazilein, hematoxylin and/or hematein. The drug is especially suited for treatment of a patient suffering from micro-circulatory disorders, diabetes mellitus, increased blood sugar values, increasing blood platelet aggregation, increased blood viscosity, decreased eryhtrocyte deformability, disorders of the lysosomal enzyme activity and/or suffering from disorders of the prostaglandin metabolism, especially increasing thromboxane $A_2$ activity.

5 Claims, 6 Drawing Sheets

DRUG, PREPARATION AND USE THEREOF

DESCRIPTION

The invention relates to a novel drug. This drug is particularly intended for the treatment of human beings.

The invention mainly concerns a drug against diabetes mellitus.

Further, the drug according to the invention is also suited to alleviate symptoms and ailments occurring in connection with or as a consequence of diabetes mellitus. In this respect, the invention relates to a drug having a prostaglandin metabolism influencing effect, in particular an effect inhibiting the formation of thromboxane $A_2$, and thus inhibiting platelet aggregation. Further, the drug according to the invention normalizes the activity of lysosomal enzymes, lowers the blood viscosity and has an effect increasing the erythrocyte deformability. On account of these effects the drug according to the invention can, for instance, be used for the treatment of arterial sclerosis, macro and micro-angiopathy and for improving micro-circulation.

Further, the invention relates to a method of preparing the drug.

Finally, the invention relates to the use of predetermined substances and mixtures of substances as active ingredients in drugs, in particular in a drug which has a prophylactic and/or therapeutic effect on micro-circulatory disorders, which can be used as an anti-diabetic, which has a blood sugar lowering effect, which has a platelet aggregation inhibiting effect, which has blood viscosity lowering effect, which has an erythrocyte deformability increasing effect, which has a lysosomal enzyme activity normalizing effect, which has a prostaglandin metabolism influencing effect and/or which has a selective thromboxane $A_2$ inhibiting effect.

In the following the invention will be explained in particular with regard to the treatment of diabetes mellitus; but this shall not constitute a limitation of the invention. On the contrary, the possibilities of application will be apparent from the following description and from the claims.

Diabetes mellitus is a generally progressing disorder of the carbohydrate metabolism as well as of the lipo-metabolism and proteometabolism due to insulin deficiency or reduced insulin effectiveness and occurs mainly in the higher age groups (diabetes type II). Typical symptoms are an excessive glucose level in the blood and/or a delayed decrease and normalization of the glucose level after eating. A typical test for early diagnosis is the glucose tolerance test (GTT). The typical examinations carried out at regular intervals after onset of the disease include the determination of the fasting blood sugar and the post-prandial sugar values.

Conventional drugs used for treating diabetes mellitus, so-called hypoglycemic agents, have a blood sugar lowering effect occurring relatively quickly, e.g. within one day after oral administration. When a chronic diabetic discontinues taking such hypoglycemic agents regularly, this diabetic will soon suffer from pathologically high blood sugar values of more than approximately 120 mg/dl.

It is the object of the present invention to provide a novel drug for treating diabetes mellitus.

It is a further object of the invention to provide a novel drug which permits the reduction of the continuous administration of hypoglycemic agents to diabetics.

It is a further object of the invention to provide a novel drug which permits the reduction of the continuous administration of hypoglycemic agents to diabetics of type II.

It is a further object of the invention to provide a novel drug which after a certain period of administration to diabetics of type II permits discontinuation of the administration of hypoglycemic agents.

It is a further object of the invention to provide a novel drug which has a micro-angiopathy preventing and/or micro-circulation improving effect, in particular by inhibiting platelet aggregation, by increasing the erythrocyte deformability, by decreasing the blood viscosity and/or by normalizing the lysosomal enzymes.

Finally, it is a further object of the invention to provide a method of preparing this novel drug.

According to the invention these objects are solved by a drug having the composition of the present invention.

According to a first aspect, the invention relates to a drug comprising as active ingredient an extract extractable from plant material of plants of the genus Caesalpinia, one or more components of this extract, and/or one or more substances present in this extract or derived therefrom but prepared synthetically.

The substances present in this extract particularly include brazilin, brazilein, hematoxylin and/or hematein.

Preferably, the drug is formulated as an orally or rectally administrable drug or as an injectable agent, e.g. in the form of a capsule having an extract content of approximately 100 to 700 mg, in particular 250 mg for orally or rectally administrable agents. Unless specified otherwise, in the following the term "the preparation" will be used for a capsule containing 250 mg of dry, powdery extract whose physiologically tolerated wall material dissolves in the gastro-intestinal tract, where it releases the extract. Preferably, an agent formulated for injection contains approximately 60 to 120 mg of active ingredient.

This extract has surprising physiological properties.

When the preparation is administered to diabetics 3 times per day—initially together with a hypoglycemic agent whose dose is however gradually decreased and the administration of which is finally discontinued entirely—a slight to good reduction of the blood sugar level will be observed mostly after approximately 14 days following the first administration. When the same dose ($3 \times 250$ mg of extract per 60 kg live weight) of the preparation is continuously administered, the blood sugar level will slowly but continuously decrease from one week to the next. After a period of approximately 2 to 12 months after commencement of the treatment, the fasting blood sugar will reach normal values below 120 mg/dl.

After a period of approximately 3 to 24 months after commencement of the treatment, the post-prandial glucose value will also reach normal values.

With progressing treatment, the glucose tolerance test will also slowly but continuously yield increasingly better values.

When all three tests—without any administration of hypoglycemic agents—have reached normal values, administration of the preparation is continued for another period of 1 to 2 months and then terminated. Without further administration of the preparation and/or hypoglycemic agents the patients' behaviour will then be normal and symptom-free provided special stress (heavy meals, overindulgence in alcohol and the like) are avoided.

In general, the drug according to the invention is effective with diabetics of type II. With insulin-dependent diabetics (type I) the drug is less effective. With such patients the additional administration of the drug according to the invention frequently permits a reduction of the otherwise required insulin doses. With some few patients there is only little effect; but these patients, too, have reported an improvement of the general awareness of life.

A series of tests have been made under the scope of the present invention in order to gain evidence of the therapeutic mechanism of the drug according to the invention. The active ingredient used for these tests was either the dried, powdery full extract extractable with water from *Caesalpinia sappan* wood, or brazilin isolated from this extract and/or synthetically prepared brazilin.

These tests confirm an increase of the peripheral action of insulin; for instance, it was possible to prove an increase of the number of insulin receptors on peripheral erythrocytes.

Based on these results, it seems that the drug according to the invention permits improved utilization of endogenous as well as of administered insulin. Obviously, this explains why after administration of the drug according to the invention to patients who depend on the administration of insulin the daily dose of insulin required for lowering the blood sugar level can be reduced.

It is well known that the glucoronic acid metabolism is activated with diabetics. Since the activity of the lysosomal enzymes (such as e.g. $\alpha$-mannosidase, $\alpha$- and $\beta$-glucosidase, $\beta$-galactosidase, $\beta$-glucuronidase, n-acetyl-$\beta$-D-glucosaminidase and the like) is not normal, especially is reduced, glycoproteins are deposited on the basilemma. This is regarded as one of the reasons of known late effects of diabetes mellitus, such as e.g. angiopathy (including micro and macro-angiopathy), arterial sclerosis and the like. The above investigations confirm an improvement of these late effects after administration of the drug according to the invention, which may possibly be attributable to an inhibition of the platelet aggregation and/or a normalization of the lysosomal enzyme activity, of which evidence has been found. This effect depends little or not at all on the blood sugar level.

It is well known that diabetics have an increased thromboxane $A_2$ level, in particular due to the activity of the thrombocytes. An increased thromboxane $A_2$ level contributes to the development of arterial sclerosis and impairs the micro-circulation by stimulating the platelet aggregation. Conventional prostaglandin synthesis inhibitors such as e.g. acetylsalicylic acid or indomethacin inhibit the activity of cyclo-oxygenase; it is true that the desired thromboxane synthetase inhibition is achieved therewith, but prostacyclin synthetase is also undesirably inhibited thereby. However, the drug according to the invention selectively inhibits only the formation of thromboxane $A_2$ without inhibiting that of prostacyclin. Thus, the drug according to the invention permits a controlled influence on the prostaglandin metabolism in the sense of an inhibition of the thromboxane $A_2$ formation. This effect was proven by means of an inhibition of the formation of malonic acid dialdehyde, wherein no influence on the formation of prostacyclin could be observed. It is well known that malonic acid dialdehyde is produced by the same enzyme system, which also causes the formation of prostacyclin and thromboxane $A_2$.

Further, diabetics typically suffer from a reduction of the erythrocyte deformability and an increase of the blood viscosity. With diabetic rats having these symptoms a significant increase of the erythrocyte deformability and a significant decrease of the blood viscosity as compared with the control group could be observed after administration of full extract from *Caesalpinia sappan* or after administration of brazilin.

According to a second aspect the invention relates to a method of preparing the drug according to the invention.

The active ingredient of the drug according to the invention is an extract which is extractable from plant material of plants belonging to the genus Caesalpinia and comprises one or several components of the extract and/or one or several substances present in this extract or derived therefrom but prepared synthetically.

The genus Caesalpinia mainly includes tropical plants, especially trees growing mainly in Central and South America and in East Asia. Representatives thereof are *Caesalpinia sappan* (sappanwood), *Caesalpinia echinata* (brazilwood), *Hematoxylon campechianum* (logwood, campechy wood), *Caesalpinia coriaria* (dividivi), *Caesalpinia braziliensis*, *Hematoxylon braziletto* and the like. It has been known from literature that these woods, which mostly are of intensive red or blue color, comprise brazilin and/or hematoxylin, which presumably are glycosidically bonded in the fresh wood. The term "plant material of plants belonging to the species Caesalpinia" particularly is to include those plants which are capable of synthesizing brazilin and/or hematoxylin. After testing of different woods of the genus Caesalpinia, particularly *Caesalpinia sappan* was used.

For obtaining the extract, one may start from fresh or dry plant material, preferably wood. Most preferably heartwood is used. The wood is chopped, e.g. rasped, and then extracted with a solvent. Common solvents are used such as e.g. water, low alcohols (such as e.g. methanol, ethanol and propanol), diethyl ethers, further high-boiling ethers (such as e.g. tetrahydrofuran and dioxane), aliphatic ketones (such as e.g. acetone or methyl ethyl ketone), aliphatic hydrocarbons (such as e.g. n-hexane or cyclohexane), chlorinated hydrocarbons (such as e.g. carbon tetrachlorides, chloroform, dichloromethane), acetylacetate and the like.

With regard to the solubility extraction is preferably carried out with a hot solvent; for instance, the slurry of the wood particles in the solvent may be reflux-cooked.

On an industrial scale, extraction with a cold solvent would also be possible, in particular when a prolonged period of extraction (e.g. several days) is provided. The solubility can also be increased by increasing the pH.

A period of extraction of several hours is suitable. To the once extracted wood, fresh solvent can be added and the extraction can be repeated once or several times. Then, the resultant liquid extracts are mixed. Finally, the solvent is removed and a dry residue is obtained which suitably is pulverized.

Particularly good results are achieved on boiling out with water; this extraction method is preferably applied. 1 part by weight of finely rasped wood, especially wood of *Caesalpinia sappan*, is mixed with approximately 10 parts by weight of neutral, deionized water and boiled with free access of air for 6 to 8 h. Subsequently, the water, which has a deep brown-red color, is drained off and the already treated wood pulp is boiled out with the same quantity of water 1 or 2 further times. The extracts are mixed, and the water is removed; suitably this can be carried out by evaporation on the hot water bath or by freeze drying. A dark-red, dry residue in an amount of approximately 2 to 10% of the wood weight is obtained. In the respective residue (full extract) brazilin and brazilein and in the full extract of some plants additionally hematoxylin and hematein can be detected by column chromatography and/or by high-pressure liquid chromatography (HPLC). The residue (full extract) is pulverized, and the resulting powder can be formulated directly in this form to an orally or rectally administrable or to an injectable drug. Preferably, capsules having a powder weight of 250 mg are produced according to common galenic methods.

Figure 1:
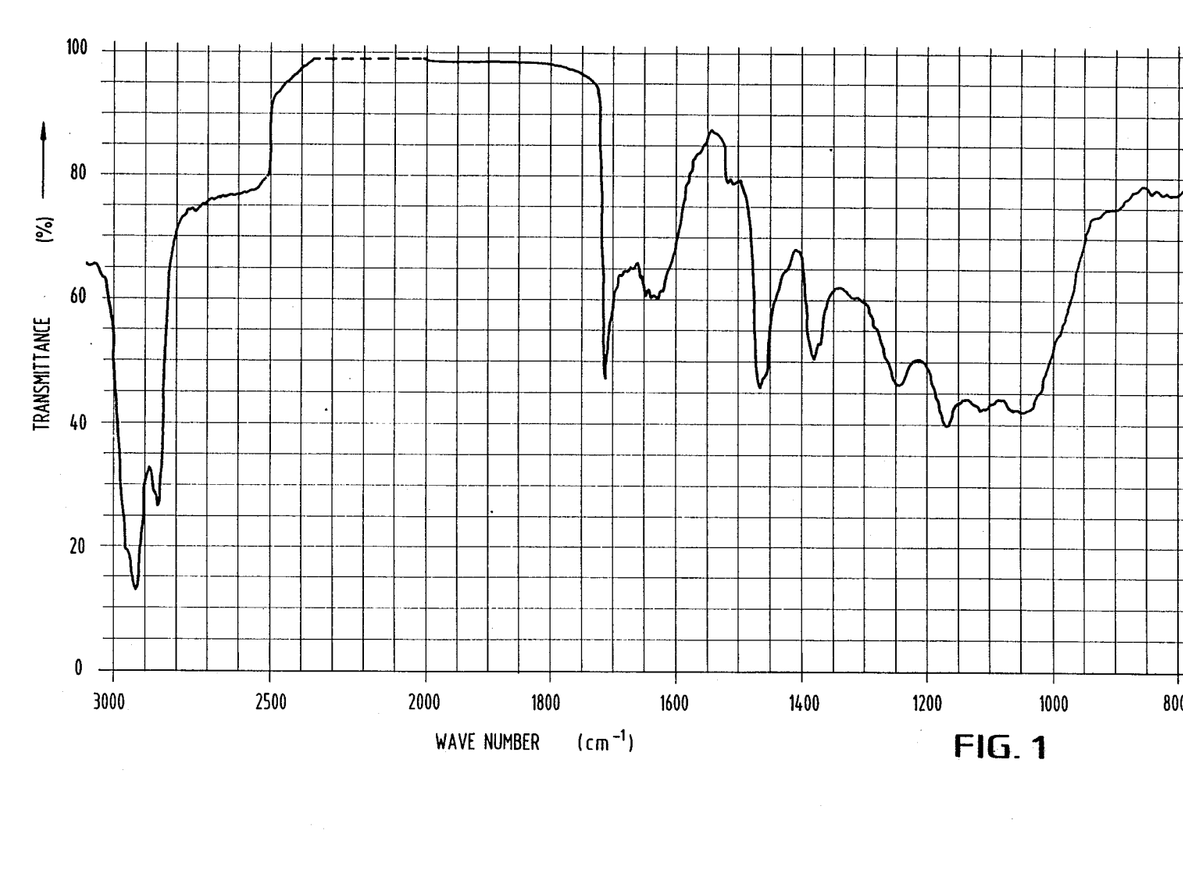

FIG. 1 shows an I.R. spectrum (KBr pellet) in the wavenumber range of 3000 to 800 cm$^{-1}$ of the dark-red powder obtained after boiling-out of sappan wood with petroleum ether.

Figure 2:
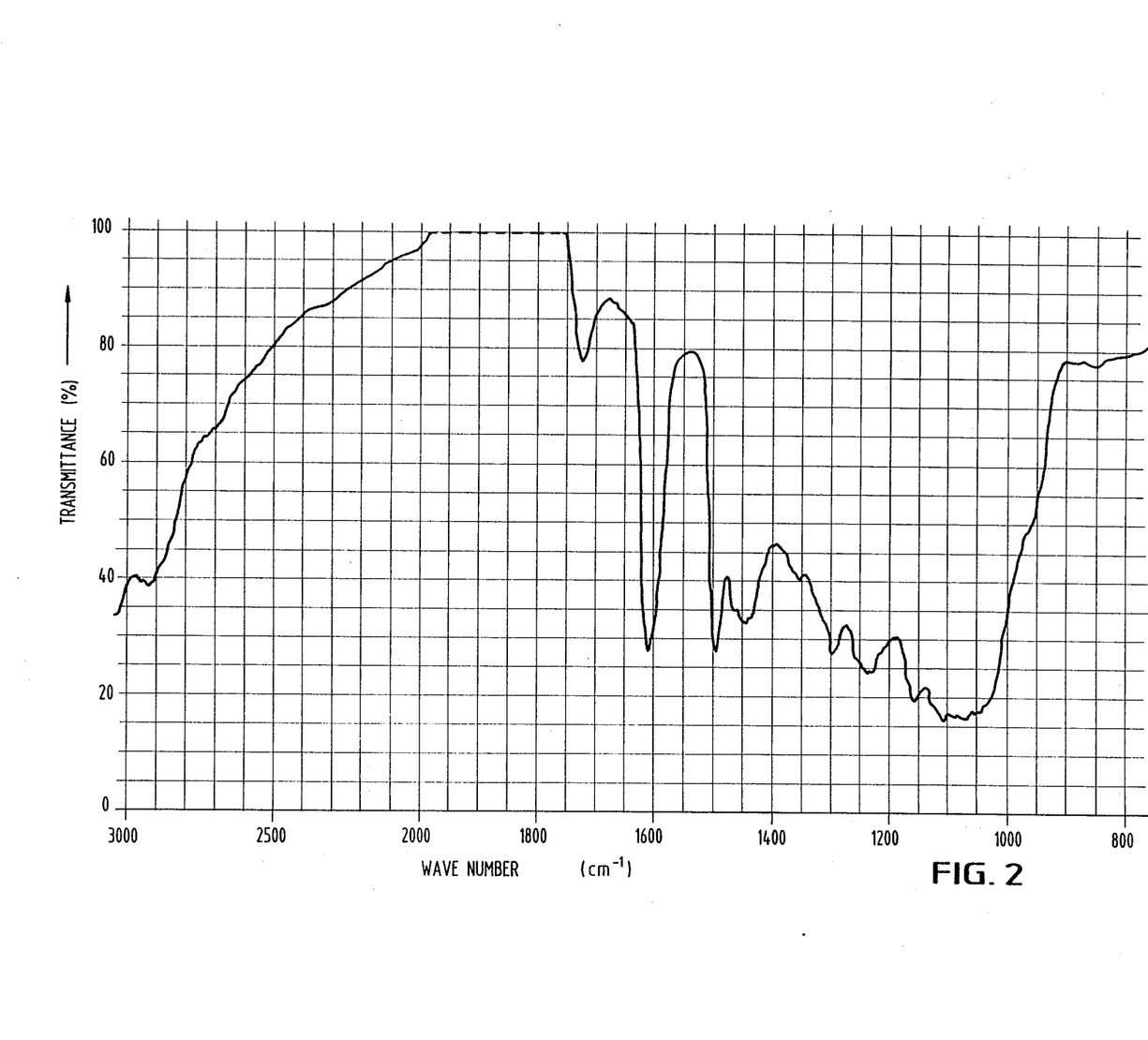

FIG. 2 shows a corresponding I.R. spectrum of the dry full extract obtained upon boiling-out of heartwood of *Caesalpinia sappan* with water.

Depending on the starting material, the extract contains approximately 1 to 5% by weight of brazilin and/or brazilein. Obviously the quinoid form of brazilein is obtained by oxidation by air under extraction conditions. From other woods such as in particular *Hematoxylon campechianum* a lower amount of brazilin is obtained, whereas the amount of hematoxylin and/or hematein obtained is larger. Test results show that the administration of synthetically prepared brazilin or synthetically prepared hematoxylin substantially has the same effects as the administration of major amounts of the full extract. Therefore, it is assumed that at least one of the active components of the full extract is a benz(b)indeno(2.1-d)pyran derivative of the following structure type (I and II, respectively)

wherein $R_1$, $R_2$, and $R_6$ may be the same or different, and represent a hydrogen group, a low alkyl group, preferably methyl group, an acetyl group, a benzyl group, or $R_1$ and $R_2$ together form a methylene group;

$R_3$ and $R_7$ may be the same or different, and represent a hydrogen group, hydroxyl group or acetyl group;

$R_4$ represents a hydrogen group, hydroxyl group, low alkyl group, preferably methyl group, an acetyl or benzyl group; and

⎯⎯ represents a single or a double bond.

The main pharmacologically active substances represented by the above general structural formula in particular include the following compounds:

(1) Brazilin, viz.
7.11b-dihydrobenz(b)indeno(2.1-d)pyran-3,6a,9,10(6H) tetrol

(2) Brazilein, viz.
6a,7-dihydro-3,6a,10-trihydrobenz(b)indeno(2.1-d)pyran-9(6H)on

(3) Hematoxylin, viz.
7.11b-dihydrobenz(b)indeno(2.1-d)pyran-3,4,6a,9,10(6H) pentol

(4) Hematin, viz.
6a,7-dihydro-3,4,6a,10-tetrahydroxybenz(b)indeno(2.1-d)pyran-9(6H)-on (5) O-triacetylanhydrobrazilin (6) O-trimethoxyindenocoumarin (7) O-trimethylanhydrobrazilan (8) O-triacetyl-cis-brazilan (9) Bis(o-triacetyl-cis-brazilan-4-yl)

wherein R = O-acetalcisbrazilan-4-yl (10) 7-hydroxy 5', 6'-methylenedioxyindeno(2',3';3,4)coumarin wherein $R_6$ = H or $CH_3$ (11) Derivatives of brazilin Trimethylbrazilin: $R_1 = R_2 = R_6 = CH_3$  $R_3$ = OH
Trimethylacetylbrazilin: $R_1 = R_2 = R_6 = CH_3$  $R_3$ = oAc
Benzylbrazilin: $R_1 = R_2 = R_6$ = benzyl  $R_3$ = OH
Benzylacetylbrazilin: $R_1 = R_2 = R_6$ = benzyl  $R_3$ = oAc (12) Desoxytrimethylbrazilin
(13) Isobrazilin ferric chloride trimethyl ether
(14) Trimethylbrazilon
(15) Trimethylbromodesoxybrazilin Hematoxylin ($C_{16}H_{14}O_6 \cdot 3H_2O$, MW 302.29+54.05) and brazilin ($C_{16}H_{14}O_5$, MW 268.29) are known substances, are commercially available (e.g. from FLUKA Feinchemikalien-GmbH, NeuUlm) and have been used especially for tinting cell preparations. Occasionally, physiological effects have also been described in scientific literature. For instance, brazilin and hematoxylin are said to have an anti-inflammatory effect (Planta Med. 31, 214–220 (1977). An antibacterial effect has also been described (Rev. Latinoam. Microbiol. 1, 225–232 (1958)). More recent discoveries have shown that brazilin and hematoxylin have an effect on the lipid peroxidation in the mitochondria of rat liver (Arch. Pharm. Res. 7, 63–64), 1984) or a plasmalipid-reducing effect on spontaneously hypertensive rats (Fette-Seifen-Anstrichmittel, 87, pp. 74–76 (1985). However, so far no drugs containing these substances have been known.

According to a third aspect the invention concerns the use of predetermined substances and mixtures of substances as active ingredient in a drug. These substances and substance mixtures are particularly suitable as active ingredient in a drug against diabetes mellitus. Further, these substances and substance mixtures are suitable as active ingredient in a drug which has a prophylactic and/or therapeutic effect on micro-circulatory disorders, which can be used as an antidiabetic, which has a blood sugar reducing effect, which has an platelet aggregation inhibiting effect, which has a blood viscosity lowering effect, which has an erythrocyte deformability increasing effect, which has a lysosomal enzyme activity normalizing effect, which has a prostaglandin metabolism influencing effect and/or which has a selective thromboxane $A_2$ inhibiting effect.

In this sense, the invention relates to a method of treating a patient who is suffering from the mentioned diseases, symptoms and/or disorders, the treatment consisting in that an effective quantity of the substances and substance mixtures specified in the following is administered to the patient.

The substances and substance mixtures which can be used in this sense include:

(A) Extracts isolable from plant material of the plants belonging to the genus Caesalpinia, including the full extracts isolable from the wood of *Caesalipinia sappan, Hematoxylin campechianum, Caesalpinia echinata, Caesalpinia coriaria, Caesalpinia braziliensis* and *Hematoxylon brazilleto*. Preferably, the extracts obtainable by boiling-out with water are used. Most preferably, the full extract is used which is obtainable by boiling out wood of *Caesalpinia sappan* with water. Further, mixtures of full extracts can be used which have been isolated from different plants of the species Caesalpinia.

(B) Benz(b)indeno(2.1-d)pyran derivatives having the following general structural formulae (I and II, respectively)

(I)

(II)

wherein
$R_1$, $R_2$ and $R_6$ may be the same or different, and represent a hydrogen group, a low alkyl group, preferably methyl group, an acetyl group, a benzyl group, or $R_1$ and $R_2$ together form a methylene group;
$R_3$ and $R_7$ may be the same or different, and represent a hydrogen group, hydroxyl group or acetyl group;
$R_4$ represents a hydrogen group or an oxo group;

$R_5$ represents a hydrogen group, a hydroxyl group, a low alkyl group, preferably methyl group, an acetyl group or a benzyl group; and === represents a single or a double bond.

The suitable benz(b)indeno(2.1-d)pyran derivatives particularly include the above-specified main pathologically active compounds (1) to (15), including brazilin, brazilein, hematoxylin and hematein, brazilin being particularly preferred.

(C) The extract which is specified in (A) and which is enriched with one or several benz(b)indeno(2.1-d)pyran derivatives mentioned in item (B), including brazilin, brazilein, hematoxylin and/or hematein, in particular brazilin.

The following test results serve for further explanation of the invention without limiting the same.

I. Preparation of Full Extract

Heartwood of *Caesalpinia sappan* was chopped. In the reflux apparatus 1 part by weight of wood was respectively extracted with 10 parts by weight of solvent for approximately 6 h. Petroleum ether, chloroform, ethanol, methanol or water was used as solvent. Subsequently, the solvent was removed by evaporation. If necessary, the wood pulp which has once been extracted may be extracted for a 2nd or 3rd time. The resultant dry, red-brown residue was pulverized and weighed. The yields obtained are shown in the following Table I, in which the percentages relate to the quantity of wood used.

TABLE 1

| Extraction with | Yields of Full Extract (%) |
|---|---|
| Petroleum ether | 0.08 |
| Chloroform | 0.11 |
| Ethanol | 2.50 |
| Methanol | 3.00 |
| Water | 7.30 |

FIGS. 1 and 2 show I.R. spectra (of the KBr pellet) of the petroleum-ether full extract (FIG. 1) and the water full extract (FIG. 2) in the wave-number range between 3000 and 800 cm$^{-1}$.

Further wood samples were extracted with boiling water and the solvent was removed by freeze drying. In this case the residue was obtained already in the form of a fine powder so that extra pulverization was unnecessary.

The resultant residues were subjected to further fractionation by different chromatographic methods (thin-film chromatography, column chromatography, high-pressure liquid chromatography (HPLC), gel filtration and the like; the fractionation always started with less polar solvents and then stronger polar solvents were used. By comparison with commercially available samples of brazilin and hematoxylin the presence of these substances in the full extract could be identified.

In the following tests the full extract obtained upon extraction of wood of *Caesalpinia sappan* with water was used. By means of known galenic methods capsules having a content of full extract of 250 mg or 500 mg and being provided with a shell which dissolves in the gastro-intestinal tract were produced from the powdery, red-brown residue.

II. Clinical Observations

Case 1:

The patient (male, age: 50, size: 166 cm, weight: 66 kg) had been treated for diabetes mellitus for 1 year. An oral, hypoglycemic agent (Diabines, a sulphonyl urea derivative) was administered to him. For 14 days a dose of 500 mg of full extract was additionally administered to him 3 times per day. Within the observation period of 44 weeks a dose of 500 mg of full extract was continuously administered to him 3 times per day. The development of the blood sugar values is shown in the following Table 2 (FBS representing the fasting blood sugar value and PC2 hBS representing the post-prandial blood sugar value 2 h after eating).

TABLE 2

| Weeks | 0 | 2 | 6 | 8 | 10 | 12 | 14 | 16 |
|---|---|---|---|---|---|---|---|---|
| FBS | 90 | 120 | | 90 | 105 | | | |
| PC2hBS | 100 | 130 | 95 | | 110 | 115 | 130 | 85 |
| Weeks | 18 | 20 | 22 | 24 | 26 | 28 | 30 | 32 |
| FBS | 120 | 110 | 90 | | | 60 | | |
| PC2hBS | | | | 100 | 96 | | 108 | 124 |
| Weeks | 34 | 36 | 38 | 40 | 42 | 44 | | |
| FBS | 95 | | | | 98 | | 80 | |
| PC2hBS | | 110 | 110 | | 118 | 105 | | |

In the course of the observation period the glucose tolerance test (GTT) also improved markedly.

Case 2:

The patient (male, age: 38, size 171 cm, weight: 62 kg) had been suffering from diabetes mellitus for at least 1 year and been treated with insulin. At the beginning of the observation period the dose amounted to 56 units of NPH insulin, it was continuously reduced (32 units in the 2nd week, 16 units in the 4th week, 8 units in the 6th week) and finally administration thereof was entirely discontinued in the 8th week. In the course of the entire observation period of 24 weeks a dose of 250 mg of full extract was administered to the patient 3 times per day. The development of the blood sugar values is shown in the following Table 3.

TABLE 3

| Weeks | 0 | 2 | 4 | 6 | 14 | 16 | 18 | 12 | 24 |
|---|---|---|---|---|---|---|---|---|---|
| FBS | 105 | | 110 | 90 | 115 | | 115 | 140 | 115 |
| PC2hBS | 220 | 190 | 160 | 130 | | 210 | 125 | | |

Case 3:

The patient (male, age: 40, size: 170 cm, weight: 66 kg) had been suffering from diabetes mellitus for at least 5 years. Initially, for 18 weeks full extract was administered to him as the sole medicine. In the 18th week administration of the preparation was discontinued. Control examinations took place in the 40th and 54th week. The blood sugar values found are shown in the following Table 4.

TABLE 4

| Weeks | 0 | 2 | 4 | 6 | 8 | 10 | 12 | 14 | 16 | 40 | 54 |
|---|---|---|---|---|---|---|---|---|---|---|---|
| FBS | 195 | 160 | 115 | 125 | 90 | 125 | 80 | 100 | 90 | 85 | 110 |
| PC2hBS | 380 | 205 | 110 | 210 | 90 | 120 | 115 | | | | |

Figure 3:
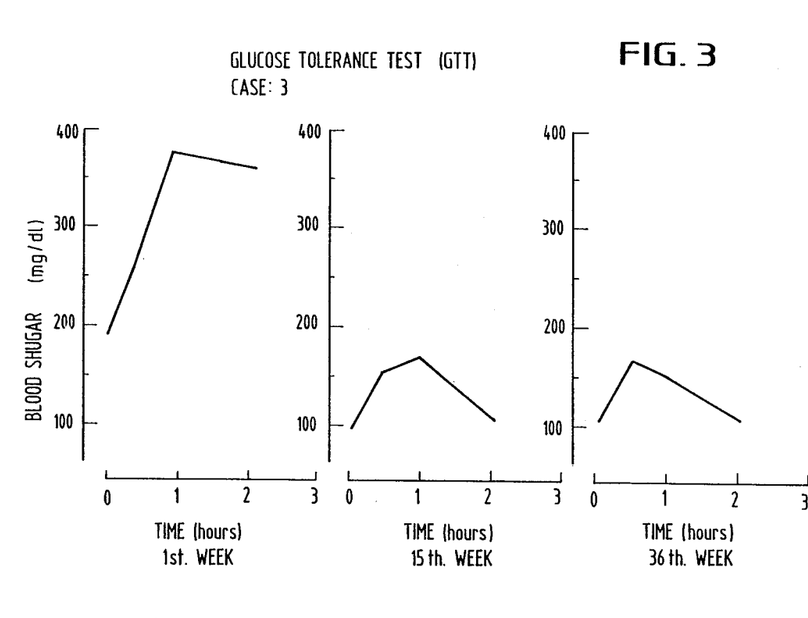

FIG. 3 is a graph of the analysis of the glucose tolerance test (GTT) in the 1st, 15th and 40th week for this patient.

Case 4:

The patient (male, age: 46, size: 173 cm, weight: 58 kg) had been suffering from diabetes mellitus for at least 1 year. Initially, for 24 weeks a dose of 500 mg of full extract was administered to him 3 times per day as the sole medicine. Thereupon, administration of the preparation was discontinued, and control examinations were made at regular intervals in the course of the following 1.5 years. The blood sugar values found are shown in the following Table 5.

TABLE 5

| Weeks  | 0   | 2   | 4   | 6   | 8  | 10 | 12  | 14  | 16  | 18 |
|--------|-----|-----|-----|-----|----|----|-----|-----|-----|----|
| FBS    | 160 | 120 | 110 | 110 | 90 | 90 | 105 | 85  |     | 90 |
| PC2hBS | 170 |     |     |     |    |    | 95  |     | 100 |    |
| Weeks  | 20  | 22  | 26  | 40  | 56 | 72 | 88  | 104 |     |    |
| FBS    | 95  | 80  | 100 | 80  | 90 | 90 | 80  | 80  |     |    |
| PC2hBS |     |     | 100 |     |    |    |     |     |     |    |

Case 5:

The patient (male, age: 41, size: 174 cm, weight: 54 kg) had been suffering from diabetes mellitus for at least 4 years. For a period of 12 weeks a dose of 500 mg of full extract was administered to him 3 times per day as the sole medicine. Thereupon, administration of the preparation was discontinued, and up to the 35th week control examinations were carried out at regular intervals. The blood sugar values found are shown in the following Table 6.

TABLE 6

| Weeks  | 0   | 2   | 4   | 8   | 10  | 16  | 22  | 28  | 35  |
|--------|-----|-----|-----|-----|-----|-----|-----|-----|-----|
| FBS    | 145 |     | 120 | 105 | 90  | 100 | 110 | 80  | 105 |
| PC2hBS | 200 | 115 | 140 |     | 100 | 105 | 105 |     |     |

By the 28th week the patient's weight had increased from initially 54 kg to 65 kg and remained unchanged from then on.

Figure 4:
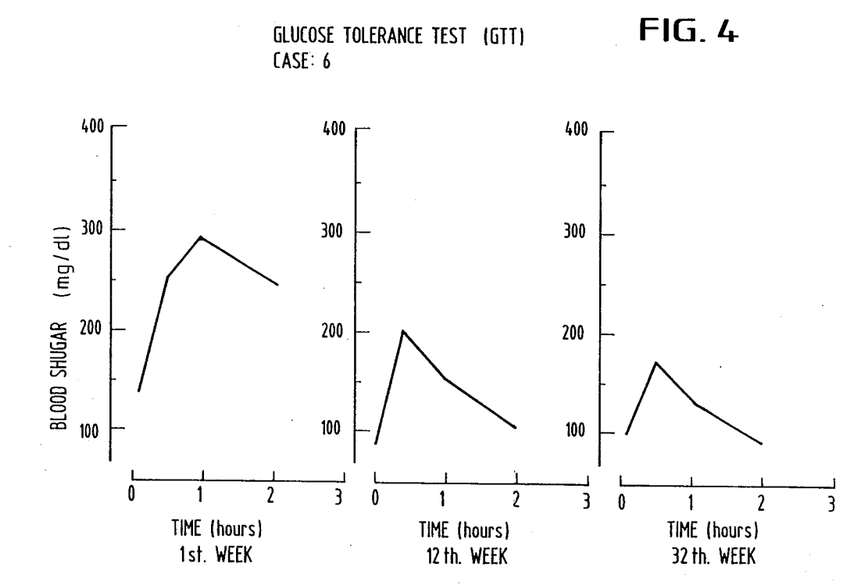

FIG. 4 is a graph of the analysis of the glucose tolerance test (GTT) in the 1st, 12th and 34th week for this patient.

Case 6:

The patient (male, age: 34, size: 165 cm, weight: 55 kg) had been suffering from diabetes mellitus for at least 1 year. During the observation period of 22 weeks a dose of 500 mg of full extract was administered to him 3 times per day as the sole medicine. The blood sugar values found are shown in the following Table 7.

TABLE 7

| Weeks  | 0   | 2   | 4   | 6   | 8   | 10  | 12  | 14  | 16  | 18  | 20  | 22  |
|--------|-----|-----|-----|-----|-----|-----|-----|-----|-----|-----|-----|-----|
| FBS    | 155 | 150 | 150 | 140 | 130 | 120 | 105 | 100 | 130 | 105 | 115 | 110 |
| PC2hBS | 340 |     |     |     | 220 |     |     | 195 |     |     | 135 | 110 |

In the course of the observation period the patient's weight increased from initially 55 kg to 60 kg.

The extraordinarily fast normalization of the blood sugar value is remarkable.

III. Blood Sugar Lowering Effect of Brazilin

By intraperitoneally administering streptozotocin (70 mg per 1 kg body weight in 0.1M of citrate buffer solution, pH 4.0) diabetes was induced in SD rats. 20 days after the injection of streptozotocin the blood sugar values of the laboratory animals were measured. The hyperglycemic rats were divided into two groups, viz. into a control group and a test group. For 10 days a dose of 110 mg of brazilin per kg body weight was daily administered to the animals of the test group. Then, the blood sugar values were measured again. The results are shown in the following Table 8.

TABLE 8

| | Blood Sugar (mg/100 ml) | |
|---|---|---|
| | 20 days after onset of diabetes | 30 days after onset of diabetes |
| Diabetic rats | 280 ± 26.8 | 337 ± 45.6 |
| Diabetic brazilin treated rats | 266 ± 16.7 | 165 ± 42.7 |
| Normal rats | | 79 ± 22.2 |
| Normal brazilin treated rats | | 77 ± 20.3 |

It will be apparent that the brazilin treatment led to a significant lowering of the blood sugar values.

IV. Increase of the Peripheral Insulin Action

Diabetic mice were divided into a control group and a test group. A dose of 100 mg of brazilin per kg body weight was daily administered to the animals of the test group; instead of brazilin, the same amount of saline solution was injected intraperitoneally to the animals of the control group.

After 30 test days, the body weight of the animals of the test group was higher and the blood sugar values of these animals were lower as compared to the diabetic animals of the control group.

On the 30th test day, the animals were made to fast for 5 h; thereupon, they were injected intravenously with 0.46 mU/g of NPH insulin. Then, the blood sugar values were measured at respective intervals of 5 min.

Figure 5:
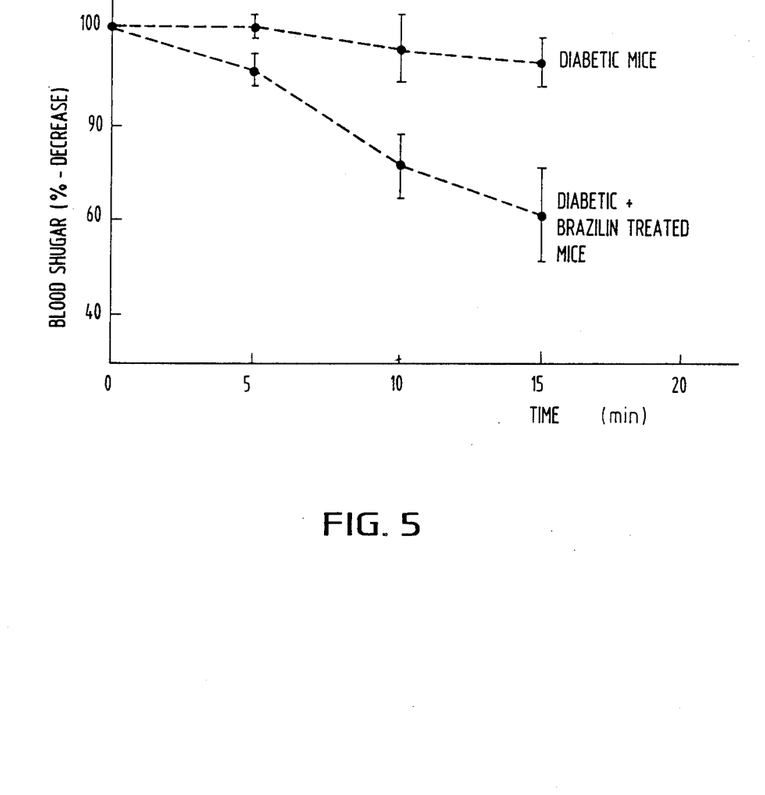

The results determined are shown in the graph of FIG. 5 (each point shown therein corresponds to a mean value of five measurements).

It will be apparent that this small dose of NPH insulin cannot significantly change the blood sugar value of the diabetic mice (control group), whereas in the mice of the test group (treated with brazilin) a marked decrease of the blood sugar values could be found.

For interpreting these findings, further tests were made with the aim to find out whether brazilin changes the affinity of the insulin receptors or can possibly increase the number of the insulin receptors.

Figure 6:
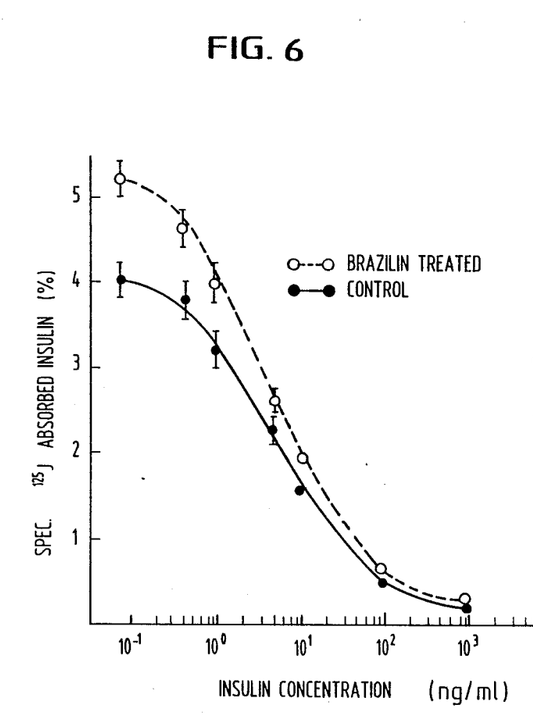
Figure 7:
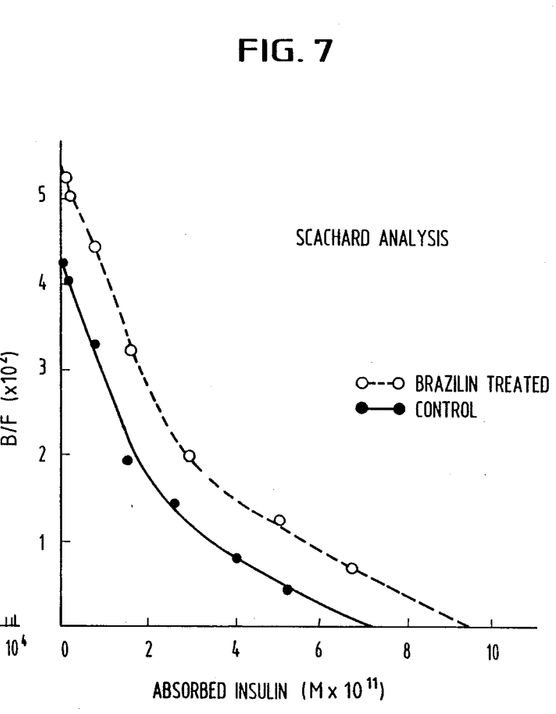

From the laboratory animals of the above-mentioned control group (diabetic mice) and the test group (diabetic brazilin treated mice) erythrocytes ($2.6 \times 10^9$/ml) were taken, $^{125}$I-insulin was bound thereto (85 pM$^{125}$I), and thereupon incubated in the presence of increasing amounts of unlabelled insulin (32 pM to 1.8 /μm) at 15° C. for 120 min. The amount of specifically bound $^{125}$I- insulin was then determined by subtracting the non-specifically bound insulin (10 ng/ml). The results obtained are shown in the graph of FIG. 6. FIG. 7 shows the scachard analysis of the binding values.

One has to conclude from the largely similar characteristic of the decrease of the specifically bound, labelled insulin for the laboratory animals of the control group and of the test group that there are no, at least no significant affinity differences but that the increased peripheral insulin action occurring upon treatment with brazilin is due to an increase of the number of the peripheral insulin receptors.

It is believed that this is why upon additional administration of brazilin or full extract the dose of insulin required by a diabetic can be reduced. In this sense, brazilin or full extract can be used as a substitute for the known sulphonyl urea derivatives or a supplement to the treatment with hypoglycemic agents, e.g. on the basis of sulphonyl urea derivatives.

V. Action of Brazilin on Postreceptor Defects

Insulin-dependent diabetes mellitus is frequently accompanied by insulin resistance. Frequently an impaired insulin action is also observed with streptozotocin induced diabetic rats. Such an insulin resistance is particularly also attributed to postreceptor defects.

With (a) untreated (normal) control animals (rats), (b) diabetic rats, and (c) diabetic brazilin treated rats glucose oxidation and lipogenesis were investigated (by means of the esterified lipids and the free fatty acids). Diabetes was induced by intravenous administration of streptozotocin (40 mg/kg live weight). Brazilin was administered intraperitoneally for 15 days (100 mg/kg body weight). Within the same period the same volume of saline solution was administered to the untreated animals of the control group.

For determining the effects of brazilin administration on the glucose oxidation, the method described by Winegard et al. (J. Biol. Chem. 233, 267 (1958)) was used, using $^{14}C$ glucose (1-$^{14}C$-glucose). The results obtained are shown in the following Table 9.

TABLE 9

Formation of $^{14}CO_2$ in fat pads isolated from rats incubated with 1-$^{14}C$-glucose (37° C.; 120 min)

| Laboratory Animals | Glucose→$CO_2$ (nmol/100 mg tissue/120 min) | |
|---|---|---|
| | Basal | Insulin stimulated* |
| Normal | 172.8 ± 21.4 (9)** | 694.2 ± 86.0 (9) |
| Diabetic | 109.1 ± 8.4 (10) | 236.6 ± 28.4 (8) |
| Diabetic + brazilin | 156.6 ± 14.7$^{(a)}$ (8) | 303.1 ± 19.0$^{(b)}$ (8) |

Remarks:
*Insulin concentration: 25 ng/ml
**Number of laboratory animals
$^{(a)}p < 0.01$ vs. diabetic control group
$^{(b)}p < 0.1$ vs diabetic control group As shown in Table 9, basal production of $CO_2$ was impaired in the fat pads of diabetic rats. With these diabetic laboratory animals the initial $CO_2$ production (=control group) can be restored to 74.6% by additionally administering brazilin. In the insulin stimulated state the action of brazilin is reduced. 14.5% of the initial $CO_2$ production are restored.

The effects of additional brazilin administration on lipogenesis were determined by means of the esterified lipids and free fatty acids formed from 1-$^{14}C$-glucose. The measurements were carried out according to established methods. The results obtained are shown in the following Tables 10 and 11.

TABLE 10

Formation of $^{14}C$—containing, esterified lipids (E.L.) in fat pads isolated from rats incubated with 1-$^{14}C$—glucose (37° C., 120 min)

| Laboratory Animals | Glucose→E.L. (nmol/100 mg tissue/120 min) | |
|---|---|---|
| | Basal | Insulin stimulated* |
| Normal | 220.8 ± 11.9 (10)** | 528.0 ± 17.8 (10) |
| Diabetic | 78.8 ± 7.7 (10) | 276.5 ± 20.8 (9) |
| Diabetic + brazilin | 113.9 ± 9.5$^{(a)}$ (10) | 326.2 ± 18.4$^{(b)}$ (9) |

Remarks:
*Insulin concentration: 25 ng/ml
**Number of laboratory animals
$^{(a)}p < 0.01$ vs. diabetic control group
$^{(b)}p < 0.1$ vs diabetic control group.

It will be apparent that with diabetic laboratory animals much less $^{14}C$ from the labelled glucose was found in the esterified lipids than with untreated laboratory animals of the control group. After all, with diabetic laboratory animals the initial production of esterified lipids from the labelled glucose (=control group) can be restored to 24.7% by additionally administering brazilin. In the insulin stimulated state brazilin also has a comparable effect. 19.8% of the initial production of esterified lipids were restored.

TABLE 11

Formation of $^{14}C$-containing free fatty acids (FFA) in fat pads isolated from rats incubated with 1-$^{14}C$-glucose (37° C., 120 min)

| Laboratory Animals | Glucose→FFA (nmol/100 mg tissue/120 min) | |
|---|---|---|
| | Basal | Insulin stimulated* |
| Normal | 3.18 ± 0.53 (6)** | 8.42 ± 1.06 (6) |
| Diabetic | 2.60 ± 0.85 (6) | 3.73 ± 0.39 (6) |
| Diabetic + brazilin | 1.83 ± 0.43$^a$ (6) | 3.39 ± 0.76$^b$ (6) |

Remarks:
*Insulin concentration: 25 ng/ml
**Number of laboratory animals
$^{a,b}$No statistically significant differences vs diabetic control group Both in the basal and in the insulin stimulated state, less $^{14}C$ from the labelled glucose is found in free fatty acids of the diabetic laboratory animals as compared to the untreated animals of the control group. In none of the two cases additional administration of brazilin has any significant effect on the production of free fatty acids.

VI. Influence on the Prostaglandin Metabolism (1) Platelet aggregation inhibiting effect of brazilin and hematoxylin The platelet aggregation was determined by a tubimetric method in a dual-channel aggregometer, assuming that a platelet-poor plasma represented 100% aggregation and that a platelet-rich plasma represented 0% aggregation. Each aggregometer tube was charged with 40 μl of platelet-rich plasma and 50 μl of test sample solution. The mixture was incubated at 37° C. for 2 min., whereupon 50 μl of ADP solution were added. Percent inhibition of the platelet aggregation caused by the test sample solution was calculated as follows:

$$\left(1 - \frac{\text{Inhibitor induced percent aggregation}}{\text{ADP induced percent aggregation}}\right) \times 100 \, (\%)$$

The following Table 12 shows the effects of an addition of brazilin or hematoxylin on the platelet aggregation of human diabetic plasma induced by 2 μM ADP.

TABLE 12

Effect of brazilin and hematoxylin on the platelet aggregation in diabetic human plasma induced by 2/μM ADP

| Conc. (M) | Tmax Aggregation (%) | Tmax Inhibition (%) | T/min Aggregation (%) | T/min Inhibition (%) |
|---|---|---|---|---|
| Control | 78.7 | 100 | 78.7 | 100 |
| Brazilin | | | | |
| $10^{-3}$ | 46.3 | 58.8 | 41.2 | 8.75 | 11.1 | 88.9 |
| $10^{-4}$ | 70.0 | 88.9 | 11.1 | | | |
| Hematoxylin | | | | |
| $10^{-3}$ | 52.5 | 66.5 | 33.5 | 7.5 | 9.5 | 90.5 |
| $10^{-4}$ | 76.3 | 96.8 | 3.2 | | | |
| Acetysalicylic acid | | | | |
| $10^{-3}$ | 70.0 | 88.9 | 11.1 | | | |
| $10^{-4}$ | 73.8 | 93.6 | 6.4 | | | |

The following Table 13 shows by means of an analogous test the effects of brazilin and hematoxylin on the platelet aggregation in normal human plasma.

TABLE 13

Effect of brazilin and hematoxylin on the platelet aggregation in normal human plasma induced by 2/μM ADP

| Conc. (M) | Tmax Aggregation (%) | Tmax Inhibition (%) | T/min Aggregation (%) | T/min Inhibition (%) |
|---|---|---|---|---|
| Control | 75.1 | 100 | | 75.1 | 100 | |
| Brazilin | | | | | | |
| $10^{-3}$ | 31.5 | 41.8 | 58.2 | 21.1 | 28.1 | 71.9 |
| $10^{-4}$ | 60.7 | 80.1 | 19.9 | 34.8 | 46.4 | 53.6 |
| Hematoxylin | | | | | | |
| $10^{-3}$ | 22.6 | 30.8 | 69.8 | 11.7 | 15.6 | 84.4 |
| $10^{-4}$ | 68.1 | 90.6 | 9.4 | 58.8 | 78.4 | 21.7 |
| Acetylsalicylic acid | | | | | | |
| $10^{-3}$ | 37.5 | 49.9 | 50.1 | 11.9 | 15.8 | 84.6 |
| $10^{-4}$ | 60.2 | 80.1 | 19.9 | 17.4 | 23.2 | 76.8 |

The test results confirm a considerable inhibition of the platelet aggregation by the presence of brazilin or hematoxylin. It will be apparent that brazilin and hematoxylin have an effect on the prostaglandin metabolism, presumably an inhibiting effect on cyclooxygenase, phospholipase $A_2$ and/or thromboxane synthetase.

(2) Inhibition of malon dialdehyde (MDA) production—without detectable influence on the prostacyclin production—by brazilin Thromboxane $A_2$ is the potent substance inducing platelet aggregation. MDA is formed through the same enzyme system as thromboxane $A_2$. Inhibition of MDA production may be due to the following factors:
(a) inhibiting action on phospholipase $A_2$,
(b) inhibiting action on cyclooxygenase,
(c) inhibiting action on thromboxane synthetase.

If an inhibiting action on MDA is detectable but no significant influence on the prostacyclin production can be detected, a selective inhibiting action on thromboxane $A_2$ may be inferred.

Rats were divided into four test groups, viz.

Group A: Normal rats (10 laboratory animals)

Group B: Normal rats (8 laboratory animals) to which an aqueous brazilin solution (comprising 110 mg of brazilin per kg body weight) was daily administered from the 20th to the 30th day Group C: Diabetic rats (8 laboratory animals; for inducing diabetes, a dose of 70 mg of streptozotocin per kg body weight in 0.1M of citrate buffer solution (pH 4.0) was administered intraperitoneally to normal rats on the 1st test day)

Group D: Diabetic rats (10 laboratory animals); for inducing diabetes, a dose of 70 mg of streptozotocin per kg body weight in 0.1M citrate buffer solution (pH 4.0) was administered intraperitoneally to normal rats on the 1st test day. From the 20th to the 30th day of the test aqueous brazilin solution (comprising 110 mg of brazilin per kg body weight) was daily administered orally to these diabetic rats. (Instead of an aqueous brazilin solution, the same amount of distilled water was administered to the laboratory animals of the groups A and C from the 20th to the 30th day.)

After expiration of the 30th test day, the test animals were sacrificed, and the MDA production was determined by means of thrombin stimulated platelets. The results obtained are shown in the following Tables 14 and 15.

TABLE 14

| Group | Body weight on 30th day | Blood sugar (mg/100 ml) on 20th day | Blood sugar (mg/100 ml) on 30th day | MDA (nmol/10 platelets) Thrombin 5,0 I. un. | MDA (nmol/10 platelets) Thrombin 1,0 I. un. | MDA (nmol/10 platelets) Thrombin 0,2 I. un. |
|---|---|---|---|---|---|---|
| A | 222 ± 17.8 (g) | | 79 ± 22.2 | 5.16 ± 2.44 | 2.46 ± 0.92 | 4.16 ± 2.04 |
| B | 226 ± 24.4 (g) | | 77 ± 20.3 | 2.20 ± 0.58 | 1.02 ± 0.48 | 0.58 ± 0.30 |
| C | 185 ± 24.4 (g) | 280 ± 26.8 | 337 ± 45.6 | 626 ± 1.36 | 3.38 ± 0.71 | 2.86 ± 0.36 |
| D | 206 ± 9.61 (g) | 266 ± 16.7 | 165 ± 42.7 | 222 ± 0.35 | 1.10 ± 0.31 | 0.76 ± 0.21 |

TABLE 15

| Laboratory Animals (rats) | 6-Keto PG F·α (ng/mg) |
|---|---|
| Normal | 0.18 ± 0.03 |
| Normal + brazilin | 0.17 ± 0.02 |
| Diabetic | 0.19 ± 0.02 |
| Diabetic + brazilin | 0.18 ± 0.03 |

It will be apparent that brazilin has an inhibiting effect on MDA production; no influence on the prostacyclin production could be observed. Therefore, this may be due to an inhibiting action on the thromboxane synthetase.

VII. Normalizing Effect on Lysosomal Enzymes

Possibly, the lysosomal glycosidases active in the kidneys are involved in the micro-angiopathy accompanying diabetes mellitus. Therefore, the lysosomal glycosidase activities upon administration of brazilin and full extract were examined.

A number of mice was divided into three groups. Group I, which was used as control group, remained untreated. To the rest of the mice diabetes was induced by administering alloxan. Part of these diabetic mice remained untreated (diabetic control group II); to the rest of the diabetic mice a dose of 100 mg of brazilin per kg body weight was administered daily. After a test period of 10 and 30 days, respectively, kidney tissue was taken from the laboratory animals and the enzyme fraction was determined. In particular, incubation was carried out for 30 min at 37° C., the reaction was stopped by adding 0.05M glycine-NaOH buffer solution (pH 10.4), centrifugation was carried out at 3000 U/min for 10 min, and the amount of p-nitrophenol formed per min and per mg of protein was determined spectrophotometrically at 410 nm at the supernatant. The results obtained are shown in the following Table 16.

TABLE 16

| Duration of treatment | Enzyme | Group I | Group II | Group III |
|---|---|---|---|---|
| after 10 days | N-acetyl-β-D-glucosaminidase | 64.51 ± 4.59 | 52.93 ± 3.55$^b$ | 60.68 ± 3.84$^D$ |
| | α-mannosidase | 8.72 ± 1.01 | 8.60 ± 1.51 | 12.49 ± 1.34$^A$ |
| | β-galactosidase | 11.53 ± 2.81 | 14.74 ± 1.97$^e$ | 12.33 ± 1.95$^E$ |
| | α-glucosidase | 4.05 ± 0.59 | 3.63 ± 0.71 | 4.62 ± 0.75$^D$ |
| | β-glucosidase | 1.25 ± 0.13 | 1.49 ± 0.31$^f$ | 1.86 ± 0.30$^E$ |
| | β-glucuronidase | 4.82 ± 0.69 | 3.33 ± 0.41$^a$ | 4.02 ± 0.65$^D$ |
| after 30 days | N-acetyl-β-D-glucosaminidase | 65.11 ± 5.37 | 57.95 ± 2.25$^c$ | 67.79 ± 4.06$^A$ |
| | α-mannosidase | 6.57 ± 0.15 | 5.69 ± 0.32$^a$ | 5.99 ± 0.54$^A$ |
| | β-galactosidase | 8.90 ± 1.26 | 7.39 ± 1.35$^e$ | 10.28 ± 0.55$^A$ |
| | α-glucosidase | 3.76 ± 0.62 | 3.33 ± 0.36 | 4.12 ± 0.40$^D$ |
| | β-glucosidase | 2.54 ± 0.35 | 2.74 ± 0.21 | 2.95 ± 0.20$^E$ |
| | β-glucuronidase | 2.26 ± 0.21 | 2.31 ± 0.13 | 2.49 ± 0.25$^E$ |

Remarks:
$^{a-f}$group I vs. group II
$^{A-F}$group II vs. group III
a. $^A$p < 0.001
b. $^B$p < 0.005
c. $^C$p < 0.01
d. $^D$p < 0.025
e. $^E$p < 0.05
f. $^F$p < 0.1

It will be apparent that the administration of brazilin has a normalizing effect on the lysosomal glycosidase activity. This aspect of the biological activity of brazilin may play an important role in preventing diabetic micro-angiopthy.

Similar results were obtained upon administration of full extracts from different plants of the species Caesalpinia. Further, these effects were found not only with alloxan induced diabetic mice but also with streptozotocin induced and with spontaneously diabetic mice.

VIII. Reduction of Blood Viscosity and Increase of Erythrocyte Deformability

Increased blood viscosity and reduced erythrocyte deformability are typical pathological states of diabetic subjects. The effect of brazilin administration to diabetic laboratory animals (rats) on the blood viscosity and erythrocyte deformability of these animals was examined.

The laboratory animals were divided into four groups; viz.
(a) untreated laboratory animals (normal);
(b) normal brazilin treated laboratory animals (normal+brazilin);
(c) merely diabetic laboratory animals (diabetic); and
(d) diabetic laboratory animals treated with brazilin (diabetic+brazilin).

For administering brazilin, the laboratory animals were daily injected intraperitoneally with a dose of 100 mg of brazilin per kg body weight for 10 days. For inducing diabetes, a dose of 175 mg of alloxan per kg body weight was administered intraperitoneally.

The blood viscosity was determined by means of heparinized blood samples relative to distilled water at 37°±0.5° C. The time interval required by 2 ml of liquid to pass between two points of a narrow glass capillary was determined. The results obtained are shown in the following Table 17.

TABLE 17

Effect of brazilin on the blood viscosity of untreated rats and diabetic rats

| Laboratory animals | Viscosity (cP) |
|---|---|
| Normal | 1.45$^a$ ± 0.08 |
| Normal + brazilin | 1.40 ± 0.06 |
| Diabetic | 1.62 ± 0.09$^b$ |
| Diabetic + brazilin | 1.52 ± 0.07$^c$ |

Remarks:
$^a$each value represents a mean value of six measurements
$^b$P < 0.01 vs. normal control group
$^c$P < 0.05 vs. diabetic control group It will be apparent that with diabetic laboratory animals the blood viscosity was significantly increased (P<0.01). No statistical differences were found between the blood viscosities of untreated laboratory animals (normal) and normal brazilin treated animals. But brazilin treatment of the diabetic laboratory animals led to a significant decrease (P<0.05) of blood viscosity. These results justify the conclusion that long-term treatment of diabetics with brazilin has a normalizing, i.e. lowering effect on the typically pathologically increased blood viscosity of diabetics.

For determining the erythrocyte deformability, the filtration rate of blood of the various laboratory animals containing approximately 4.9×10$^{12}$ erythrocytes per 1 was determined under common, standardized conditions. The results obtained are shown in the following Table 18.

TABLE 18

Effect of brazilin on the erythrocyte deformability of untreated and diabetic rats

| Laboratory animals | Filtration rate (ml/min) |
|---|---|
| Normal | 22.9$^a$ ± 0.3 |
| Normal + brazilin | 23.1 ± 0.3 |
| Diabetic | 17.4 ± 0.1$^b$ |
| Diabetic + brazilin | 19.6 ± 0.4$^c$ |

Remarks:
$^a$each value represents a mean value of six measurements
$^b$P < 0.01 vs. untreated control group
$^c$P < 0.01 vs. untreated and vs. diabetic control group

It was found that brazilin has no effect on erythropoesis. The blood of alloxan diabetic rats had a significantly lower filtration rate (P<0.01) than that of untreated rats; with regard to the test conditions, a reduced erythrocyte deformability has to be inferred therefrom. Brazilin treatment did not signficantly influence the filtration rate of the blood of the otherwise untreated control group. But with diabetic animals brazilin treatment caused a significant increase of the filtration rate; this has to be regarded as an indication of increased erythrocyte deformability. These results justify the conclusion that long-term treatment of diabetics with brazilin has a normalizing, i.e. increasing effect on the typically pathologically reduced erythrocyte deformability.

I claim:

1. A method of treating a patient suffering from diabetes mellitus, which comprises administering to said patient an amount effective for treating said diabetes mellitus of a pharmaceutical composition comprising as active ingredient a benz(b)indeno(2.1-d)pyran derivative represented by the following structural formula (II)

(II)

wherein $R_1$ and $R_6$ may be the same or different, and represent a hydrogen group, a lower alkyl group, an acetyl group, a benzyl group, or $R_1$ and $R_6$ together form a methylene group;

$R_3$ and $R_7$ may be the same or different, and represent a hydrogen group, hydroxyl group or acetyl group; $R_4$ represents a hydrogen group or an oxo group; $R_5$ represents a hydrogen group, a hydroxyl group, a lower alkyl group, an acetyl group or a benzyl group; and ═══ represents a single or a double bond.

2. The method of claim 1 wherein said active ingredient is brazilein.

3. The method of claim 1, wherein said active ingredient is hematein.

4. The method of claim 1 wherein said active ingredient is an extract obtainable from wood of *Caesalpinia sappan.*

5. The method of claim 1 wherein said active ingredient is brazilein or hematein, said pharmaceutical composition is administered orally or rectally in capsule form containing about 100 to 700 mg of said active ingredient or by injection wherein said composition contains about 60 to 120 mg of said active ingredient.

* * * * *